(12) United States Patent
Duhot et al.

(10) Patent No.: US 7,166,766 B1
(45) Date of Patent: Jan. 23, 2007

(54) METHOD FOR PRODUCING BRANCHED FATTY ACIDS USING GENETICALLY MODIFIED PLANTS

(75) Inventors: Pierre Duhot, Herblay (FR); Eric Gontier, Germiny (FR); Daniel Thomas, Villers-sur-Coudun (FR); Brigitte Thomasset, Compiègne (FR); Marc Menard, Compiègne (FR)

(73) Assignee: Total Raffinage Distribution S.A., Puteaux (FR)

( * ) Notice: Subject to any disclaimer, the term of this patent is extended or adjusted under 35 U.S.C. 154(b) by 0 days.

(21) Appl. No.: 09/542,546

(22) Filed: Apr. 3, 2000

(51) Int. Cl.
*C12N 15/82* (2006.01)
(52) U.S. Cl. .................................................. 800/281
(58) Field of Classification Search ................ 800/281, 800/287, 298, 312, 320, 320.1; 435/69.1, 435/320.1; 536/23.2
See application file for complete search history.

(56) References Cited

U.S. PATENT DOCUMENTS 5,110,732 A * 5/1992 Benfey et al. ............ 435/172.3
5,936,139 A * 8/1999 Schmid ....................... 800/281
5,959,178 A * 9/1999 Fritig

FOREIGN PATENT DOCUMENTS

FR    WO 91 14670 A    10/1991
FR    WO 96 03511 A    2/1996

OTHER PUBLICATIONS

De Luca, "Molecular characteriztion of secondary metabolic pathway", 1993, AgBiotech News and Information, vol. 5, No. 6, pp. 225N-229N.*
Broun et al, "Catalytic Plasticity of Fatty Acid Modification Enzymes Underlying Chemical Diversity of Plant Lipids", 1998, Science vol. 282, pp. 1315-1317.*
Van De Loo, "An oleate 12-hydroxylase from *Ricinus communis* L. is a fatty acyl desaturase homolog", 1995, Proc. Natl. Acad Sci, vol. 92, pp. 6743-6747.*
Schmid K.: "Dihydrosterculate in tobacco transformed with bacterial cyclopropane fatty acid synthase," Plant Lipid Metabolism, 1995, pp. 108-110, XP002068786.
Ohlrogge J.: "Design of new plant products: Engineering of fatty acid metabolism," Plant Physiology, vol. 104, 1994, pp. 821-826, XP002068787.

* cited by examiner

*Primary Examiner*—Elizabeth F. McElwain
(74) *Attorney, Agent, or Firm*—Venable LLP; Michael A. Gollin; Nancy J. Axelrod (57) ABSTRACT

The invention relates to plant cells comprising a recombinant nucleic acid coding for a product which induces or stimulates the synthesis of branched fatty acids in said cells. It also relates to a production process for branched fatty acids using these plant cells or plants containing it.

8 Claims, 9 Drawing Sheets

METHOD FOR PRODUCING BRANCHED FATTY ACIDS USING GENETICALLY MODIFIED PLANTS

The present invention relates to a production process for fatty acids. It relates more particularly to a production process for fatty acids with a non-linear aliphatic chain. The process of the invention consists more particularly in the use of genetically modified plants. The fatty acids thus produced, in a free or bound form, possibly modified chemically or enzymatically, may be used in the manufacture of various industrial products, in particular lubricants of the motor oil or hydraulic oil type.

The fatty acids are acids with an aliphatic chain of a length usually included betweeen 6 and 25 carbon atoms. The aliphatic chain may be linear or non-linear (also designated branched). The fatty acids produced naturally exist in either the free or an esterified form, in particular in the form of diglycerides or triglycerides. The fatty acids are usually used in various types of industries, in particular for the preparation of lubricant bases of natural origin or in detergents, adjuvants or even in the constitution of biocarburants. For all of these applications, it is particularly advantageous to be able to use fatty acids of natural origin, in particular derived from plant material. Thus, different production and extraction processes for fatty acids from plants (in particular from plant seeds) have been described in the prior art (see in particular Harrington et al., Ind. Eng. Chem. Prod. Res. Dev. 1985, vol. 24, page 314; FR 2 722 798). Moreover, the application WO 94/13814 relates to plant cells genetically modified by an enzyme implicated in the transfer of free fatty acids to cholesterol. Nonetheless, although this application allows the composition of the triglycerides to be modified, it in no way allows the structure of the aliphatic chain of the fatty acids to be altered. Schmid K. (Plant Lipid Metabolism (1995, 108) mentions the synthesis of cyclic fatty acids (dihydrosterculate) in genetically modified tobacco cells. However, this document does not described the production of branched fatty acids, or corresponding means or industrial applications.

One of the major disadvantages of the earlier processes using plants consists precisely in the low diversity of the fatty acids which may be obtained. Thus, basically, the plants naturally produce fatty acids with a linear aliphatic chain of the C6 to C24 type. Now, the studies conducted by the applicant Company have shown that to obtain a good lubricant base, it is particularly advantageous to use fatty acids with a non-linear (branched) aliphatic chain. Thus the applicant has shown that the use of (free or bound) fatty acids with a branched aliphatic chain led to products of the lubricant type being obtained which exhibit good thermal stability, good resistance to oxidation, good viscosity, good biodegradability as well as low melting points (or pour points).

There thus exists a real need to have available processes making it possible to produce branched fatty acids efficaciously. The present invention provides an advantageous solution to precisely these needs by describing processes based on the genetic modification of plants.

Thus, a first feature of the invention relates to a production process for branched fatty acids by means of genetically modified plants.

Another feature of the invention lies in genetically modified plants capable of producing branched fatty acids and in a production process for such plants. Another feature of the invention also consists of plant cells containing a recombinant nucleic acid coding for a product which induces or stimulates the synthesis of branched fatty acids in said cell.

The present invention also relates to the recombinant nucleic acid such as defined above and to any vector containing it.

DETAILED DESCRIPTION OF THE INVENTION

The present invention thus relates to a production process for branched fatty acids from genetically modified plants, to plants and cells of genetically modified plants producing branched fatty acids as well as to recombinant nucleic acids and vectors containing them, which can be used for this purpose.

In the sense of the invention branched fatty acid means any fatty acid possessing a true branched aliphatic chain. As emerges from the text of the present application, the term "branched" designates in the sense of the invention fatty acids bearing one or more substitutions at one or more distinct positions of the aliphatic chain. Thus, the sole presence of a ring in the aliphatic chain is insufficient to qualify the fatty acid as branched according to the invention. It is preferably a fatty acid possessing a C6 to C24 aliphatic chain, and even more preferably a C12 to C24 aliphatic chain. Examples of such acids, essentially in a saturated form and not yet branched, are in particular capric acid (C10), lauric acid (C12), myristic acid (C14), palmitic acid (C16), stearic acid (C18), eicosanoic acid (C20), docosanoic acid (C22), tetracosanoic acid (C24) and mixtures of these latter. The aliphatic chain of the branched fatty acids of the invention may be branched at one or more positions by different groups. Advantageously, the aliphatic chain bears one to four branches located in the central part of the aliphatic chain and/or in its terminal part opposite to the acid function. More preferably, the branch(es) is (are) located on one or more carbons included between the positions 8 and 15 of the aliphatic chain. Moreover, the branched group may be any alkyl group, preferably a C1 to C5 alkyl, still more preferably methyl, ethyl, propyl, isopropyl, butyl, tert.butyl. A particularly preferred branched group is a methyl group. Particular branched fatty acids in the sense of the invention are, for example, 9-methyl octadecanoic acid; 10-methyl octadecanoic acid; 9,12-dimethyl octadecanoic acid; 10,12-dimethyl octadecanoic acid; 9,13-dimethyl octadecanoic acid; 10,13-dimethyl octadecanoic acid; 9,12-dimethyl oleic acid; 10,12-dimethyl oleic acid; 9,13-dimethyl oleic acid; 10,13-dimethyl oleic acid or even 2,4,6,8-tetramethyl decanoic acid.

Moreover, the branched fatty acids according to the invention may be branched fatty acids in the free form or in the form of derivatives. They may be in particular branched fatty acid esters, such as monoesters, diesters or triesters of glycerol (triglyceride). In the case of di- or triglycerides, it is moreover not necessary that all of the fatty acids present in the molecule be branched. Thus, a triglyceride may contain 1, 2 or 3 branched fatty acids. It is, however, preferable that the proportion of branched fatty acids in the esters or other derivatives be high.

A first object of the invention relates more particularly to a production process for branched fatty acids, characterized in that said branched fatty acids are produced from at least one plant cell or from one plant material or from a plant comprising at least one cell, said plant cell comprising in its genome a recombinant nucleic acid coding for a product inducing or stimulating the synthesis of branched fatty acid(s).

In the sense of the invention "recombinant nucleic acid" designates any ribonucleic or deoxyribonucleic acid constructed by genetic engineering techniques. It may be in particular a complementary DNA, a genomic DNA or a messenger RNA. Such a nucleic acid may be of varied origin, in particular bacterial, viral, plant, mammalian, synthetic or semi-synthetic. A recombinant nucleic acid may be prepared by using the procedures known to the specialist skilled in the art, and in particular by screening of nucleic acid libraries with suitable probes, by chemical synthesis (by using nucleic acid synthesizers), by enzymatic digestions/ligations, etc or by any combination of these methods.

The present invention may be used with different types of plants, preferably plants cultivated in fields. Advantageously, it is an oleaginous plant, such as for example colza, sunflower, peanut, soya, flax or even maize. It may also be a tobacco plant.

The plant cells according to the invention may be the cells of any of the plants such as defined above. It may more preferably be a cultivatable plant cell and capable of regenerating a plant.

The term "plant material" designates any part of a plant such as defined above, comprising at least one cell. It may be any tissue of said plant such as, in particular, seeds.

The cell or plant according to the invention is thus genetically modified, so that it comprises in its genome, in a free or integrated form, a recombinant nucleic acid coding for a product inducing or stimulating the synthesis of a branched fatty acid. The plants and plant cells of the invention thus comprise fatty acids, a fraction of which is constituted by branched fatty acids. Depending on the applications envisaged, it may be advantageous for this fraction to represent a substantial proportion of the total fatty acids. Advantageously, the recombinant nucleic acid is present in the cell in a form integrated into the genome of said cell, so as to be segregationally more stable.

A product is designated as inducing the synthesis of a branched fatty acid when it allows the plant cell containing it to accomplish a synthesis which it could not have done in its absence. One speaks of a product stimulating the synthesis of a branched fatty acid when it is a product which allows the plant cell containing it to promote a preexisting synthetic pathway in said cell but one exploited little or not at all by the latter, for example, for reasons of substrate stoichiometry or specificity. The recombinant nucleic acid used in the present invention may code more particularly for a product capable of inducing a branching of the fatty acids produced by the cell post-synthesis or for a product enabling a branching concomitant with said synthesis to be achieved. Moreover, these two approaches may be combined.

The fatty acids are synthesized in the chloroplasts of the plant cells. This synthesis comprises several repetitive cycles during which carbon units are added successively to each other to generate the fatty aliphatic chain. After being synthesized these linear fatty acids are exported to the cytoplasm where they undergo various post-synthetiic (or post-elongation) modifications and, in particular, a desaturation by enzymes designated desaturases.

In a first embodiment of the invention, the recombinant nucleic acid codes for a product making it possible to induce or stimulate the post-synthetic branching of the fatty acids produced by said plant cell. More particularly, according to this first embodiment of the invention, the recombinant nucleic acid codes for an enzyme permitting the transfer of one or more alkyl groups to the double bonds of the unsaturated fatty acids.

The alkyl groups transferred may be, as indicated above, any alkyl group preferably comprising from 1 to 5 carbon atoms. They are advantageously alkyl groups comprising from 1 to 3 carbon atoms and in particular methyl, ethyl, propyl or isopropyl.

Advantageously, the recombinant nucleic acid codes for a heterologous enzyme, i.e. an enzyme derived from an organism other than a plant cell. More particularlly, the enzyme used is advantageously derived from a prokaryotic or eukaryotic microorganism such as, for example, a bacterium or a yeast.

As an illustration of the recombinant nucleic acids according to the invention, mention may be made of a recombinant nucleic acid coding for cyclopropane fatty acid synthase, also designated CFAS. The nucleic acid may also code for methyl transferases such as, for example, SAM-methyl transferases, i.e. enzymes capable of catalyzing the transfer of a methyl group from SAM (S-adenosyl-methionine) to an unsaturated fatty acid or, more generally, to a doouble bond of an aliphatic chain. A particular recombinant nucleic acid in the sense of the invention codes, for example, for the cyclopropane fatty acid synthase such as described by Wang et al. (Biochemistry 31 (1992) 11020) or any enzyme analogous to this latter. The term "analogous" in the sense of the present invention means any enzyme possessing one or more structural modifications compared to the enzyme describe above and conserving an alkyl group transfer activity towards the double bonds of an aliphatic chain. These structural modifications may be mutations, deletions, substitutions or additions of one or more amino acids. The term "analogous" also comprises the homologous sequences obtained from other organisms. Another "analogue" is an enzyme produced by a nucleic acid hybridizing with all or part of the sequence of the transferase or synthase and conserving an activity of the same kind. The hybridization is advantageously performed under conditions of normal or, preferably, high stringency. Stringent hybridization conditions are, for example: hybridization at 42° C., 50% formamide, 5×SSC, 1× Denhardt; washing at 65° C. with 0.1× SSC, 0.1% SDS. Non-stringent hybridization conditions are, for example: hybridization at 37° C., 40% formamide, 5×SSC, 1× Denhardt; washing at 50° C. with 1×SSC, 0.1% SDS. The stringent conditions are particularly suited when the test nucleic acid is present in low amounts and/or in an only slightly purified form. The non-stringent conditions are more suitable when the test nucleic acid is present in larger amounts and in a form significantly represented in the sample. Other hybridization conditions are well known to the specialist skilled in the art (see, in particular, Maniatis et al.) Another particular example of recombinant nucleic acids according to the invention is a recombinant nucleic acid coding for the methyl transferase responsible for the synthesis of 9-methyl-10-hexadecenoic acid in *Corynebacterium* spp. (Niepel et al., J. Bact. 180 (1998) 4650) or in a variety of alga (Carballeira et al., Lipids 32 (1997) 1271).

Moreover, this embodiment consisting of transferring an alkyl group to an aliphatic chain requires that alkyl groups or alkyl donors are present in said cell. In this respect, the cell reserves for methyl group transfer are constituted principally by the SAM group. Consequently, for the purpose of improving still further the efficacy of this reaction, and hence of the yield of branched fatty acids, a particular embodiment consists of introducing into the plant cell a second nucleic acid coding for an enzyme implicated in the synthesis of the alkyl donor, in addition to the nucleic acid coding for the product defined above. Preferably, it is a nucleic acid coding for an enzyme involved in the synthesis of SAM. Even more preferably, it is a nucleic acid coding for SAM synthetase or an analogue of the latter. This nucleic acid may be introduced by the intermediary of a second recombinant nucleic acid, simultaneously or sequentially with respect to the first. According to another embodiment, the nucleic acids coding for the two enzymes are borne by the same recombinant nucleic acid.

According to a second embodiment of the present invention, the recombinant nucleic acid contained in the plant cell codes for a product making it possible to induce or stimulate the incorporation into the aliphatic chain of a fatty acid during its elongation groups generating one or more branches. Accordingly, this second approach does not involve a post-synthetic modification of the fatty acids produced but achieves branching concomitantly with said synthesis.

Figure 1:
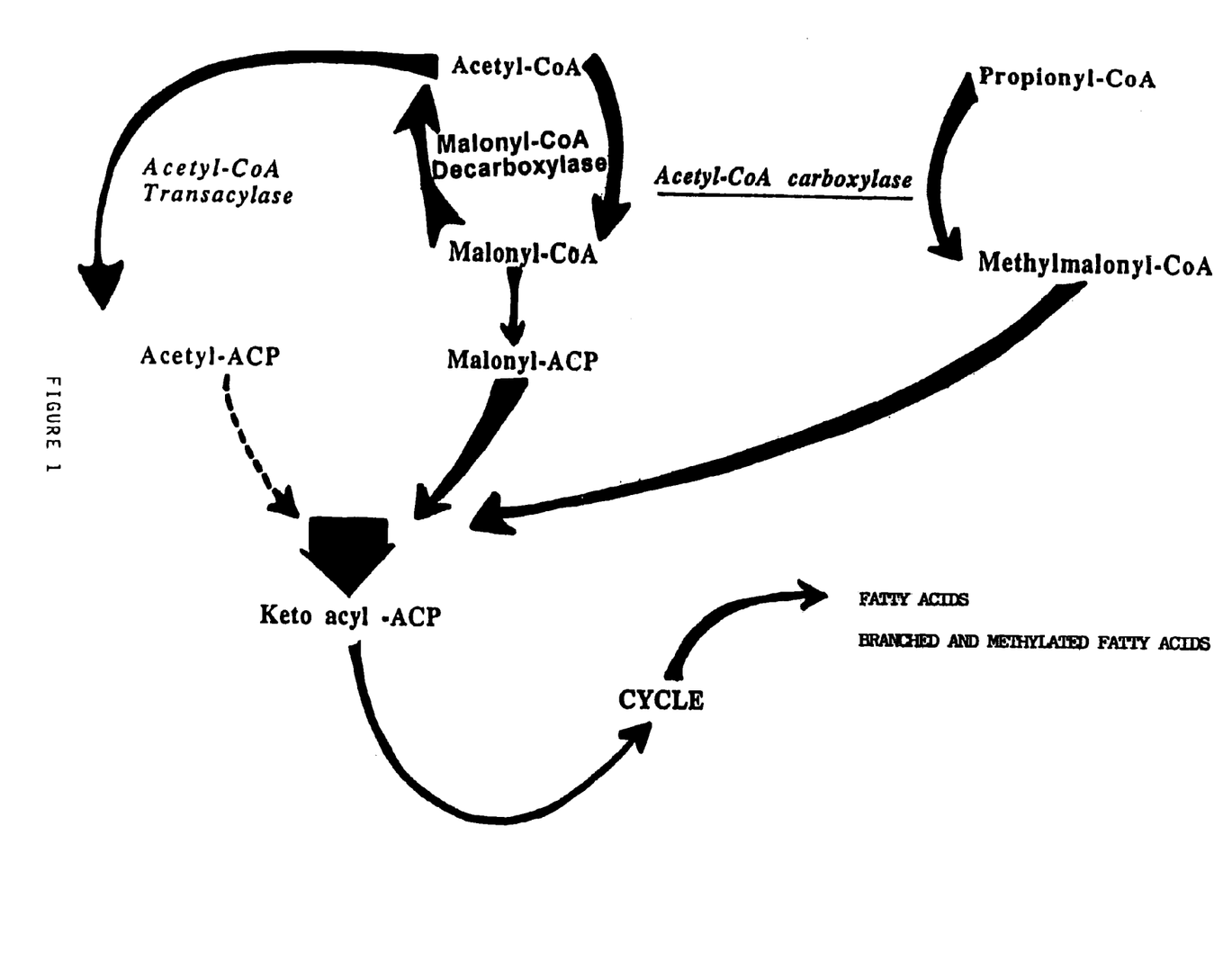
FIG. 1: Schema of the synthesis of fatty acids in the chloroplast of the plant cell.

This embodiment is preferably obtained by forcing the plant cell to use as substrate for the synthesis of the aliphatic chain an acyl-CoA group bearing more than 3, and preferably between 4 and 8, carbon atoms instead of malonyl CoA. Advantageously, the substrate used is a non-linear acyl-CoA group. Even more preferably, it is a non-linear acyl-CoA group permitting the incorporation of an odd number of carbon atoms into the aliphatic chain during its elongation. This strategy enables branched fatty acids called multi-branched fatty acids to be obtained, such as for example 2,4,6,8-tetramethyldecanoic acid. A particular example of an acyl-CoA type substrate is for example methylmalonyl CoA. Methylmalonyl CoA is a non-linear group, bearing 4 carbon atoms, three of which serve for elongation. In this case, for the purpose of forcing the plant to use this substrate for the synthesis of the aliphatic chain, it is particularly advantageous to introduce into the plant cell a recombinant nucleic acid coding for a malonyl CoA decarboxylase (E.C. No. 4.1.1.9). The mode of action of this enzyme as well as in a more general manner the synthetic pathway of the branched fatty acids by the cells modified according to this strategy is shown in FIG. 1. It is understood that any other enzyme analogous to that mentioned above and capable of forcing the plant to use an acyl-CoA bearing more than 3, and preferably 4 to 8, carbon atoms as substrate in the synthesis of the aliphatic chains of the fatty acids may be used in the present invention. As a particular example of such enzymes, mention may be made in particular of the malonyl CoA decarboxylase, the nucleotide sequence of which has been described in the literature (cf. the examples) as well as any analogue of the latter.

This second embodiment may also be obtained by modifying the specificity of the enzymes implicated in the synthesis of the fatty aliphatic chain, in particular by modifying the specificity of the enzyme which prevents the transfer of malonyl CoA to malonyl ACP, and in particular the specificity of all or part of the fatty acid synthase, acetyl CoA carboxylase or acetyl CoA transacylase. In this respect, the fatty acid synthase consists of a multi-enzyme complex and the modification of its specificity may be obtained by modification of one, several or even all of the subunits.

Moreover, as indicated above, these two embodiments may be combined to generate plant cells capable of synthesizing fatty acids with a branched aliphatic chain both during and after elongation.

For the implementation of the present invention, the recombinant nucleic acid advantageously comprises regulatory regions of the promoter type which are functional in plant cells and which enable the expression of the nucleic acids defined above to be regulated. Among the regulatory regions of transcription which can be used in plants and in the implementation of the present invention, mention may be made for example of the regions associated with the cauliflower mosaic virus (35S, 19S) or the promoter regions of structural genes such as the genes for nopaline synthase (nos) or octopine synthase (ocp) or mannopine, agropine or acyl carrier protein (ACP). The structure and cloning of these different regions have been described in the literature. More generally, any promoter permitting constitutive, spatial or temporal expression of a nucleic acid in a plant cell may be used for the implementation of the present invention. In this respect, it is possible in particular to use promoters which permit expression localized to certain tissues or parts of the plant (seed, pollen, etc.), or promoters whose activity depends on the stage of development of the plant (elongation, flowering, etc.). As a promoter which is expressed predominantly in the seeds, mention may be made, for example, of the ACT promoters of ACP and napine or the promoters described by Krebbers et al. (Plant Physiol. 87 (1988) 859). The use of such promoters may prevent any potential side effect induced by a generalized and massive production of branched fatty acids in the plant, and also facilitate the recovery of the fatty acids thus produced, by concentrating them in certain regions of the plant.

Moreover, it is also advantageous to introduce into the recombinant nucleic acids according to the invention terminating sequences localized at 3' which may derive either directly from the gene used or arise from other gene regions such as those in particular of nopaline synthase (nos) or also octopine synthase (ocp), mannopine, agropine or ACP.

The recombinant nucleic acid which thus advantageously comprises a regulatory region of transcription, a gene or region coding for an active product such as defined above and 3' terminating regions is advantageously introduced into a plasmid cloning or expression vector.

In this respect, another object of the invention relates more particularly to a recombinant nucleic acid comprising:

a nucleic acid coding for a product such as defined above, a promoter regulating the expression of said nucleic acid and capable of causing the localized expression of this nucleic acid in certain plant tissues or certain plant parts, and a 3' transcription termination region.

More particularly, the promoter comprised in the genetic constructions of the invention is a promoter capable of causing the expression of the nucleic acid localized in the seed of the plant. The term "localized expression" signifies that the expression is markedly greater in the tissue concerned than in the other plant tissues. Nonetheless, it is understood that an absolute specificty of expression is not required, provided that a significant expression is observed in the tissues selected. The localized character of expression according to the invention is doubly advantageous because it facilitates, on the one hand, the recovery of the branched fatty acids and because it limits the risks of toxicity (in particular on good growth and reproduction) of the products expressed in the modified plants.

The recombinant nucleic acids of the invention may, moreover, comprise address signals which lead to improvement in addressing the proteins synthesized to the cell compartments where they exert their activity. When the product synthesized is a product implicated in the transfer of alkyl groups to fatty chains post-elongation, the protein exerts its activity in the cytoplasm and thus does not require special address signals. When the product is implicated in the synthesis of the fatty chains itself, it exerts its activity within the chloroplasts and it may be advantageous to use a signal which addresses this product to the chloroplast. Such signals are known in the prior art.

Another object of the invention relates to a recombinant nucleic acid comprising:
- a nucleic acid coding for a methyl transferase capable of catalyzing the transfer of a methyl group to an aliphatic chain of an unsaturated fatty acid,
- a functional promoter in the plant cells regulating the expression of said nucleic acid, and
- a 3' transcription termination region.

In another particular embodiment, the object of the invention is a recombinant nucleic acid comprising:
- a nucleic acid coding for a malonyl CoA decarboxylase,
- a functional promoter in the plant cells regulating the expression of said nucleic acid, and,
- a 3' transcription termination region.

Another object of the present invention also relates to a vector comprising a recombinant nucleic acid such as defined above. Such a vector may be in particular a derivative of the vector Ti. The vectors of the invention may be used to produce large quantities of recombinant nucleic acids in the cells or to produce the corresponding enzymes or to transform plant cells.

The present invention also relates to any plant cell comprising a recombinant nucleic acid or a vector such as defined above.

The recombinant nucleic acids or vectors of the invention may be introduced into the plants by any technique known to the specialist skilled in the art, and in particular by chemical, physical or biological procedures. The chemical techniques implicate for example the use of transfecting agents which facilitate cellular penetration. The physical techniques are, for example, electroporation, bombardment, "gene guns", etc. A well-known and particularly efficacious biological technique consists of using infiltrations under vacuum or co-culture, viral vectors and, preferably, *Agrobacterium tumefaciens* which enables genetic material to be introduced into the plant cell by means of the plasmid Ti. These techniques are well-known to the specialist skilled in the art. After transformation, the plant cells actually containing the nucleic acid according to the invention are selected. The cells may then be maintained in culture, possibly multiplied in culture and used directly for the production of branched fatty acids (batch cultures, fed batch, etc.). These cells may also be stored for subsequent use. These cells may also be used to regenerate transgenic plants, according to standard procedures used in plant biology.

Thus, another object of the invention relates to a process for the preparation of a transgenic plant capable of producing branched fatty acids, comprising the introduction of a recombinant nucleic acid such as defined above into a plant cell or plant part and the regeneration of a transgenic plant from these plant cells or plant parts. Advantageously, the introduction is achieved by using *Agrobacterium*. In a particular embodiment, the introduction is made into plant cells or foliar disks. The introduction is performed by any technique known to the specialist skilled in the art.

Another object of the invention relates to a transgenic plant, the cells of which contain a recombinant nucleic acid such as described above and which codes for the enzymes permitting the post-synthetic branching of the fatty acids produced by said plant cell to be induced or stimulated, or sequences inducing or stimulating the incorporation of branched groups into the aliphatic chain of a fatty acid during elongation.

The transgenic plants of the invention contain the recombinant nucleic aid stably integrated into the genome of both germ cells and somatic cells.

The invention also relates to any plant material derived from such a plant, and in particular to the seeds.

The invention also relates to a production process for branched fatty acids by culture of a cell such as defined above and recovery of the fatty acids produced.

The invention also relates to a production process for branched fatty acids by cell culture of a plant cell comprising:
- the culture of these cells in a medium suitable for their growth,
- the extraction and purification of the branched fatty acids from the cell biomass, and in particular from these cells or from the supernatant of said culture.

The invention also relates to a preparation process for branched fatty acids by extraction from a transgenic plant, the cells of which contain a recombinant nucleic acid such as defined above according to which said fatty acids are recovered from any part of said plant, and in particular from the seeds of said plant.

The invention relates to a preparation process for branched fatty acids from a transgenic plant, the cells of which contain a recombinant nucleic acid comprising:
- the field culture of said transgenic plants;
- the recovery of the seeds of said plants;
- the extraction of the fatty acids from these seeds.

The process of the invention is quite especially suited to the production of non-cyclic methylated fatty acids, in particular C16 or C18 fatty acids bearing one or more methyl groups. As preferred examples mention may be made of 9-methyl octadecanoic acid, 10-methyl octadecanoic acid, 9-methyl hexadecanoic acid and 10-methyl hexadecanoic acid.

In the production processes for branched fatty acids such as defined above, an optional treatment step of the fatty acids may be performed in order to improve still further the physicochemical properties of these compounds. Thus, the processes of the invention comprise in particular:
- an extraction step of the branched fatty acids from the cells, seeds or plants, and,
- a treatment step of the fatty acids to improve their physicochemical properties.

The extraction may be performed by the standard methods known to the specialist skilled in the art mentioned above.

More preferably, the treatment step is a hydrogenation step, performed under standard or forcing conditions, leading to the formation of saturated branched fatty acids. More specifically, the hydrogenation may be performed under the conditions described by Christie W. W. (Topics in Lipid Chemistry, 1970, vol. 1, F. D. Gunstone, ed. London: Logus Press)—incorporated into the present description by reference—, optionally in the presence of a palladium catalyst.

More generally, the invention relates to the use of a transgenic plant regenerated from a cell such as defined above for the production of branched fatty acids.

The invention also relates to the use of a plant or part of a transgenic plant, at least some of the cells of which contain a recombinant nucleic acid such as defined above for the production of branched fatty acids.

Finally, the invention relates to branched fatty acids capable of being obtained by the process such as that described above. The inventors have shown in particular that the branched fatty acid esters such as defined in the invention have good resistance to oxidation and low pour points, and thus possess advantageous properties for use as lubricants.

Hence, the invention relates to the use of branched fatty acid esters such as defined above as lubricants, in particular for the preparation of oil compositions, in particular motor oil and hydraulic oil, in particular by replacing unconventional or synthetic bases (such as esters, polyalphaollefins, etc.).

The invention also relates to a lubricantt composition comprising branched fatty acids such as described above and one or more additives such as in particular anti-wear agents, pressure modifiers, surfactants, etc.

The present application will be described in more detail with the aid of the examples which follow, which must be considered as illustrative and non-limiting.

LEGENDS TO FIGURES

FIG. 2: Representation of a recombinant nucleic acid comprising a gene coding for a transferase under the control of the promoter CaMV 35S (FIG. 2A) or nos (FIG. 2B).

EXAMPLE A

Construction of a Genetically Modified Plant Cell Capable of Producing Branched Fatty Acids by Post-Elongation Alkylation This example illustrates the construction of genetically modified plants capable of producing branched fatty acids by post-elongation methylation. In particular this example describes the insertion into the genome of the plant by genetic engineering of a gene or a set of genes coding for:

on the one hand, one or more transferases, for example, methylases or methyltransferases (of the cyclopropane fatty acid synthase type i.e. CFA synthase, for example) capable of catalyzing the addition of methyl groups (or other alkyl groups: ethyl, propyl, isopropyl . . . ) to the double bonds of unsaturated fatty acids; and, on the other, one or more genes leading to an increase in the pool of methyl donor groups (S-adenosyl methionine i.e. SAM), in particular of the gene coding for S-adenosyl methionine synthetase (SAM synthetase).

The construction of these transgenic plants according to the invention is achieved according to the following steps.

Step 1: Plant Material Used.

The tobacco model plants of the SR1 type (Horsch et al., 1985 Science, 22, 1229–1231) or BY2 type (Nagata et al., 1992 Int. Rev. of Cytol., 132, 1–30) are used for the initial experiments. In fact, these two model species can be easily transformed by *Agrobacterium tumefaciens* (Van Lisjsebettenns et al., 1986, J. Mol. Biol. 188, 129–145; Shaul et al. 1986; Shaul et al., 1996 Proc. Natl. Acad. Sci. USA, 93, 4868–4872) and permit the regeneration of novel plants. All oleaginous plants such as colza, sunflower, peanut, soya, maize, etc may naturally be used in the same manner.

Step 2: Genic Constructions

Figure 2A:
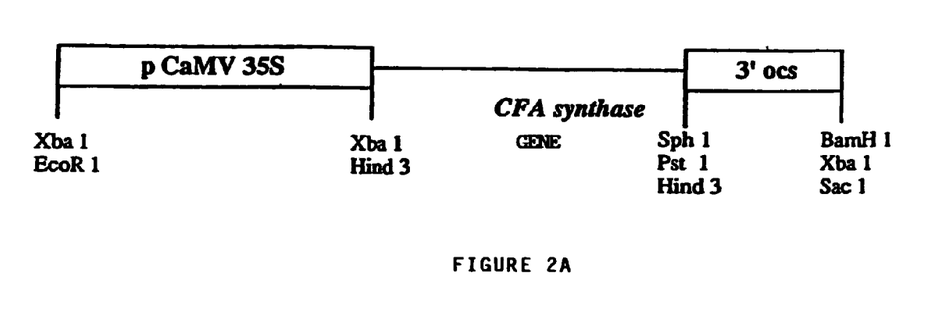
Figure 2B:
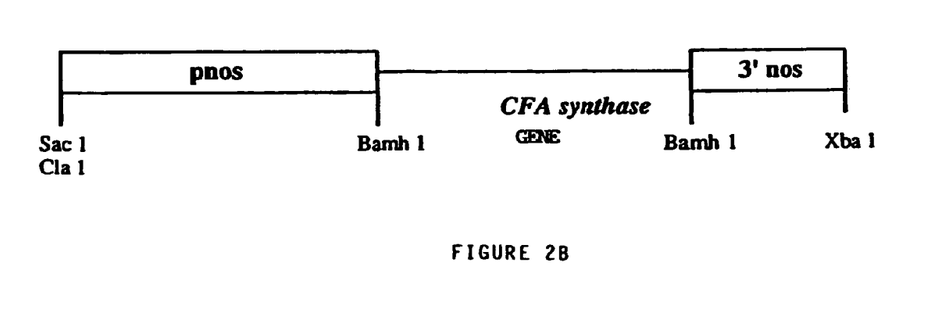
Figure 3:
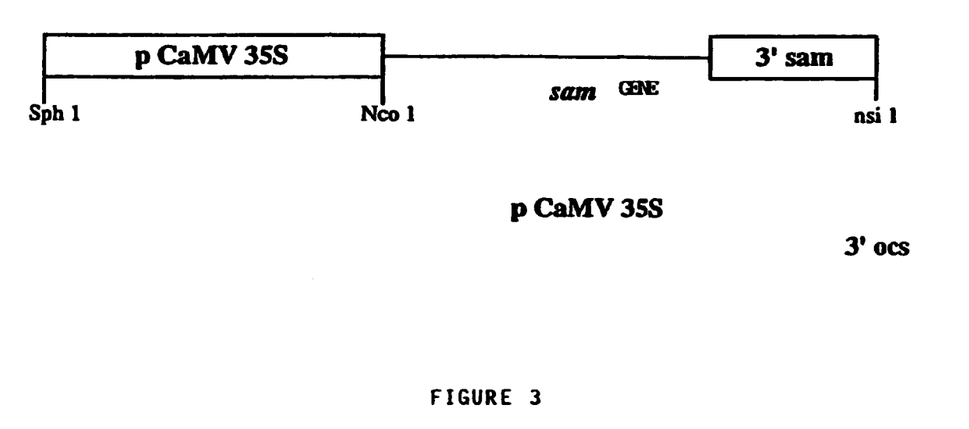
FIG. 3: Representation of a recombinant nucleic acid comprising a gene coding for SAM synthase.

The genetic transformation consists of introducing a recombinant nucleic acid comprising an expression cassette including the gene to be transferred, the expression promoter for this gene which will be able to permit constitutive, spatial or temporal expression, and a 3' transcription termination region. In what follows the various genetic elements used and the construction of the corresponding recombinant nucleic acids are described (FIGS. 2 and 3).

2.1. Selection and Isolation of the Nucleic Acids Coding for the Enzymes.

In this example use is made of nucleic acids coding for methylases or methyltransferases derived from prokaryotic or eukaryotic organisms and the coding sequences of which are analogues of the coding sequence of the cyclopropane fatty acid synthase described by Wang et al. (1992 Biochemistry, 31, 11020–11028). More particularly, a nucleic acid coding for cyclopropane fatty acid synthase is isolated and its sequence verified.

Moreover, to improve the efficacy of the process, in a particular embodiment, a second nucleic acid may be used coding for the SAM synthetase whose nucleotide sequence has been described by Peleman et al. (1989 Plant Cell, 1, 81–93).

2.2. Selection of the Promoter Regions.

For the construction of the recombinant nucleic acids, different types of promoters may be used and, in particular, any promoter functional in plants and permitting the regulation of gene expression.

In this respect, mention may be made of the promoters permitting localized expression in the seeds (or certain seed tissues) of plants such as in particular the promoter of the gene coding for prolamine (Zhou et al., Transgenic Res. 2 (1993) 141), the promoter of the gene coding for the pea lectin (Pater et al., Plant J. 6 (1994) 133), the promoter of the gene coding for the LEA ("Late Embryogenesis Abundant protein") (Goupil et al., Plant Mol. Biol. 18 (1992) 1049), the promoter of the gene coding for the family of the napin proteins (NAP) (Boutilier et al., Plant Mol, Biol. 26 (1994) 1711), the promoter of the gene coding for rice gluterin (Zxhao et al., Plant Biol. 25 (1994 429), the promoter of the gene coding for olesin (Keddie et al., Plant Mol. Biol. 19 (1992) 443), the promoter of the gene coding for the S family of storage proteins (2S promoter of the napA gene, 11S or 12S promoter of the globulin gene), the promoter of the gene coding for betaphaseolin, legumin, gamma conglutin, concanavalin A, desaturase Bn10 (Plant Physiol. 104, 1167), wheat alpha/beta gliandin, rice catalase CatA, sorgo alphakafirin or also maize Adh 1 (Kyozuka et al., Plant Cell 6 (1994) 799) or pea SBP65 protein (Dehaye et al., Plant Mol. Biol. 65 (1997) 605).

In this example the promoters used are the 35S promoter of cauliflower mosaic virus and the promoter of the nopaline synthase (nos) gene. The structure of these promoters has been described for example by Benfey and Chua (1990, Science, 250, 959–966).

2.3. Selection of the Transcription Termination Regions.

In this example, the transcription terminating regions used are derived either directly from the gene used (FIG. 3) or from the genes for nopaline synthase (nos) and octopine synthase (ocs).

2.4. Construction of the Recombinant Nucleic Acids (Vectors).

In order to construct the recombinant nucleic acids enabling the above elements to be introduced into plant cells, these genetic elements are first isolated and subcloned in cloning vectors of the pBR322 and pUC types which bear markers permitting the selection of the transformants which become resistant to cytotoxic agents such as antibiotics, toxins, etc. The expression cassettes are then introduced into binary vectors containing the sequences necessary for the transformation of the plants, in particular the T-DNA vector. This vector is used for the transformation of the plants and the structure of the vectors containing the specific recognition sequences (RB and LB) has been widely described in the literature (Book by Hoekema, the Binary Plant Vector Systems, Offsetdrukkerij Kanters B. V., Alblasserdam, 1985. Molecular Genetics of the Bacteria-Plant Interaction, Puhler A., Ed., Sprinnger-Verlag, NY, 1983. Plant Genetic Transformation and Gene Expression: A Laboratory Manual Draper J., Scott R., Armitage P. and Walden R. Eds, Blackwell Scientific Publications, Oxford, 1988. Kahl G. and Weising K. (1993) Genetic Engineering of Plant Cells. In Biotechnology: Genetics Fundamentals and Genetic Engineering. Rehm H. J., Reed G., Pühler A and Stadler P. Eds, VCH Publishers Inc., New York (USA) vol. 2, pp 547–659).

The structure of the recombinant nucleic acids thus prepared is shown in FIGS. 2 and 3.

In another particular example the binary vector pTDEcfa was constructed as follows.

a) Clonage and Characterization of the cfa Gene Coding for the Cyclopropane Fatty Acid Synthase.

Figure 4:
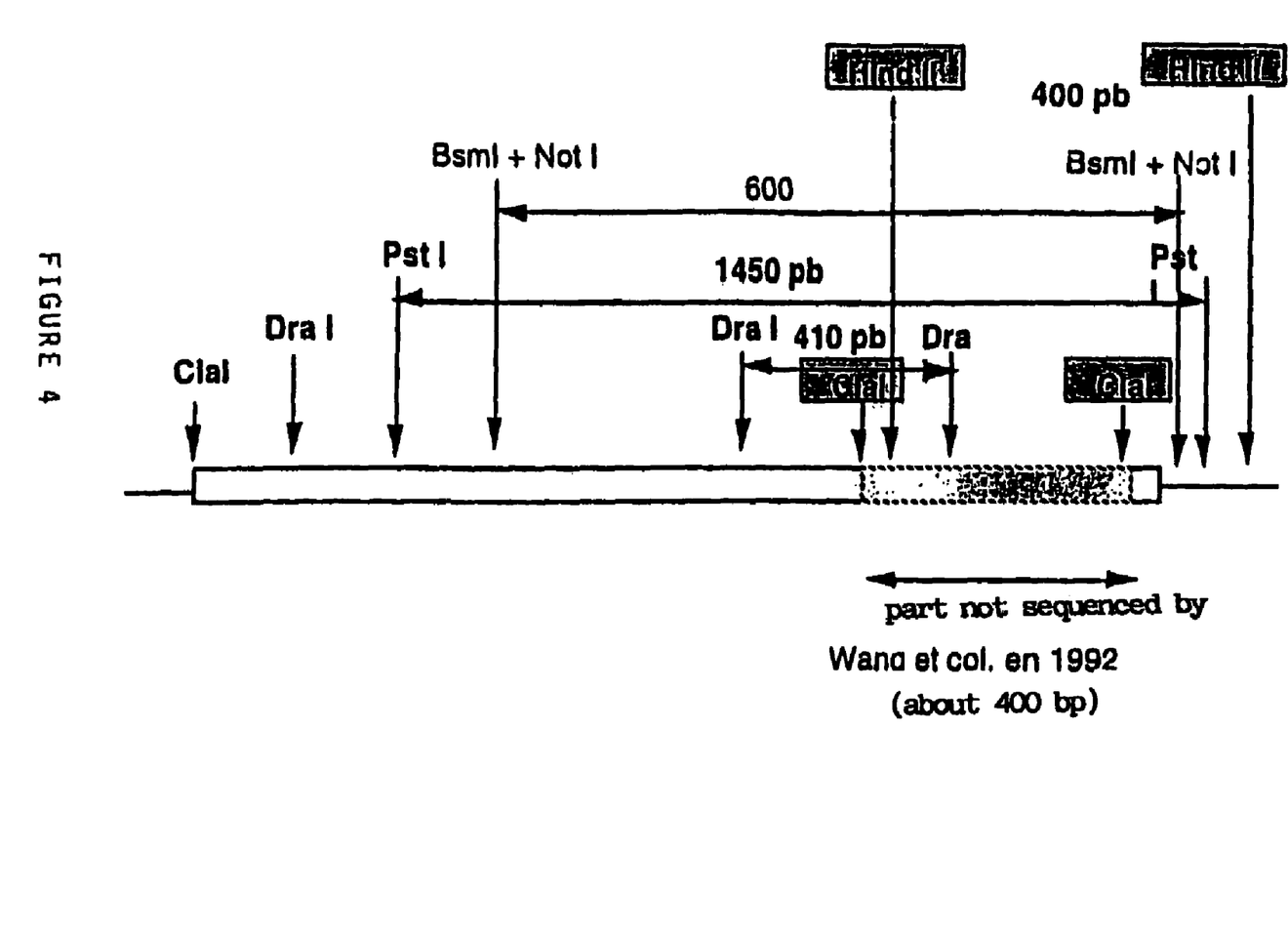
FIG. 4: Restriction map of the cfa gene.

On reading the article by Wang (Wang et al., 1992) an ambiguity was noted concerning the size of the ClaI fragment present in the plasmid pAYW19. Furthermore, in the sequencing strategy Wang et al. (1992) present the ClaI fragment with a unique restriction site for the enzyme HindII upstream from the ClaI site. Now, according to the published sequence this site appears downstream from the ClaI site. Hence, as a first step, verification of the integrity and characterization of the entire structure of the cfa gene were undertaken. For this purpose, a restriction map of the cfa gene present in the plasmid pAYW19 was constructed with different restriction enzymes. The analysis of the sizes of the fragments obtained after restriction, agarose gel electrophoresis and staining of the fragments with ethidium bromide made it possible to draw the physical map of this gene, which is shown in FIG. 4. These results were confirmed by sequencing of the fragment downstream from the HindII site. The complete and corrected sequence of the cfa gene was computerized and introduced into a software program (DNA strider) for study of the restriction sites.

b) Construction of the Binary Vector pTDEcfa

This example describes the construction of the binary vector pTDEcfa bearing the expression cassette of the corrected cfa gene, flanked by the LB and RB regions of the plasmid Ti. This binary vector makes possible the transfer, by A tumefaciens, of said cassette into the genome of the plant cells.

i) Construction of the Plasmid pBSgus

The plasmid pBSgus was constructed by cloning the EcoRI-HindII fragment derived from the binary vector pTDE4 in the vector pBS (pBluescript, BRL) which only contains very few restriction sites. The EcoRI-HindII fragment contains the p35S promoter and the 3'nos terminator. Thus the vector formed, pBSgus, contains the unique restriction sites for the enzymes NcoI and NruI. These two enzymes allow the gus gene to be isolated while maintaining the integrity of the regulatory sequences (p35S and 3'nos).

ii) Creation of the Expression Cassette of the Corrected cfa Gene.

Figure 5:
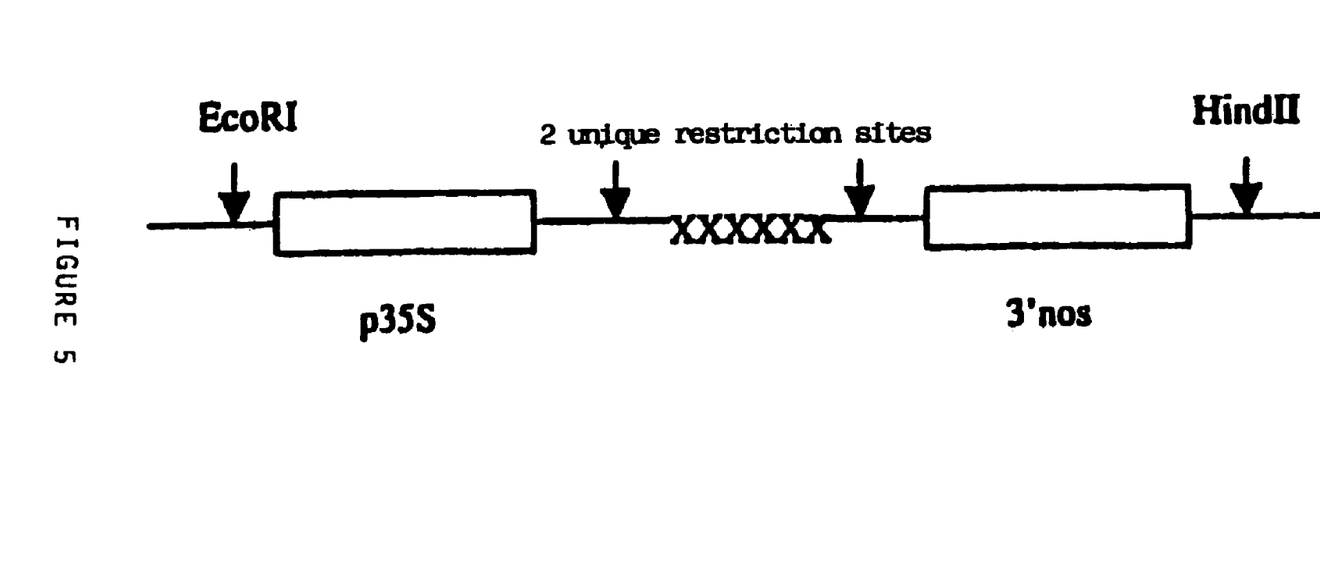
FIG. 5: Representation of a regulation cassette of a gene capable of stimulating the production of branched fatty acids.
Figure 6:
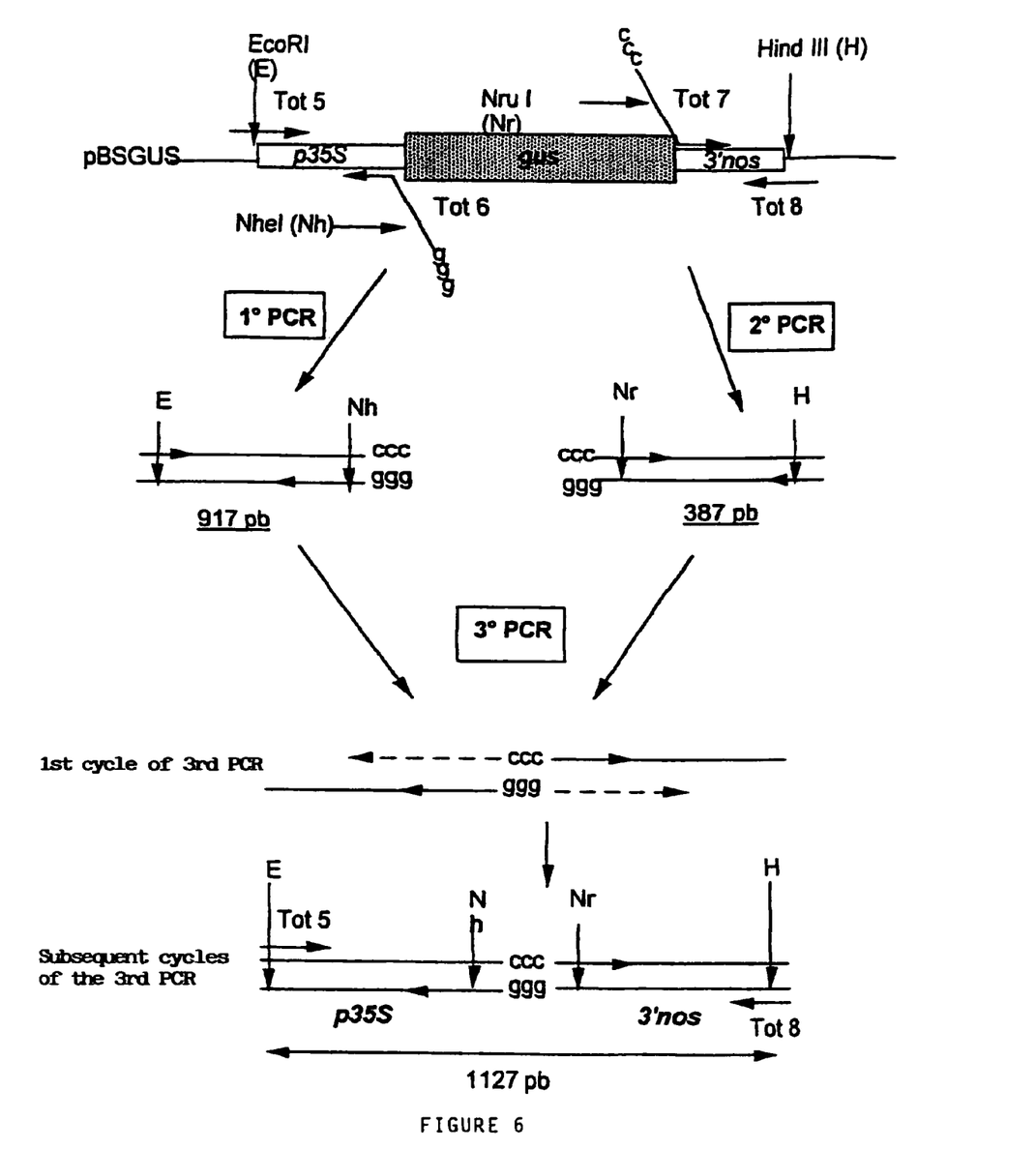
FIG. 6: Construction scheme for the regulation cassette of the cfa gene.

The principle of this step is based on the replacement of the gus gene of the plasmid pBSgus by a cloning site comprising unique sites. This cassette was created by PCR starting from pBSgus and contains the p35S promoter and the 3'nos terminator. The primers necessary for the PCR were selected so as to create the structure shown in FIG. 5. The choice of the two unique restriction sites is determined by the need for them to be absent from p35S, 3'nos, the cloning vector into which the structure will be integrated and from the cfa gene which will be integrated between the 2 regulatory sequences. After analysis of the different sequences, two possible sites were identified: NheI and NruI. The construction of the cassette was achieved as follows (FIG. 6):

Cloning of the regulatory cassette in the pGEM-T in order to obtain the vector pGEM(35S-3'nos)

Creation by PCR of the NheI site upstream and the NruI site downstream from the cfa gene.

Cloning of the PCR product in the vector pGEM-T in order to obtain the vector pGEMcfa Sequencing of the vectors pGEM(35S-3'nos) and pGEMcfa.

Cloning of the NheI-NruI fragment derived from the vector pGEMcfa in the vector pGEM(35S-3'nos) from which the NheI-NruI fragment has been eliminated. The vector obtained by this cloning is designated pEM(35S-cfa-3'nos).

Starting from the vector pGEM(35S-cfa-3'nos) it is possible to isolate a unique EcoRI-HindII fragment containing the sequence (35S-cfa-3'nos).

After optimization of the PCR conditions for the creation of the regulatory cassette (FIG. 6), the latter was cloned in the vector pGEM-T. Thus, after analysis by restriction with different enzymes the vector pGEM(35S-3'nos) is available in two clones.

Similarly, the vector pGEMcfa was obtained and two clones were selected.

The desired sequence of the vectors pGEM(35S-3'nos) and pGEMcfa was computerized, then introduced into the software program DNAstrider. Two clones for each vector were sent by express mail to the Genome company to be sequenced.

The results of the sequencing were obtained for the two clones (2 and 3) theoretically containing the vector pGEMcfa. After alignment with the theoretical sequence, the sequence of the vector contained in clone 2 exhibits several mutations and hence it will not be possible to use this clone for further study. The sequence of the vector contained in clone 3 contains a mutation, however this mutation is a so-called "silent" mutation because it will have no effect on the sequence of the CFA protein.

The results concerning clone 3 containing the vector pGEM(35S-3'nos) are not very encouraging because the vector contained in this clone exhibits several mutations. However, these mutations are relatively remote from the sequences essential for the correct functioning of the p35S promoter and the 3'nos terminator. Moreover, clone 4 could not be sequenced. A new selection was thus made from the clones containing the vector pGEM(35S-3'nos) and clone 10 was selected for sequence analysis.

Thus, the vector pGEM(35S-3'nos) contained in clone 10 was sequenced. The method of sequencing by PCR was used with 3 primers (T7, SP6 and a primer close to the poly CCC sequence). The sequence obtained was compared to the theoretical sequence. The 2 errors detected just before the HindIII site seem to be errors in the theoretical sequence and not in the sequencing, since they are found in the sequences of the vectors pGEM(35S-3'nos) contained in clones 3 and 4 sequenced previously.

On the basis of the sequence results, the Nhel-Nrul fragment derived from the vector pGEMcfa contained in clone 3 was cloned in the vector pGEM(35S-3'nos) contained in clone 10 at the Nhel and Nrul sites. The vector obtained was designated pGEM(35S-cfa-3'nos). Among the clones obtained a selection was made using several restriction enzymes. We selected clone 13 for further cloning.

iii) Construction of the Binary Vector

Figure 7:
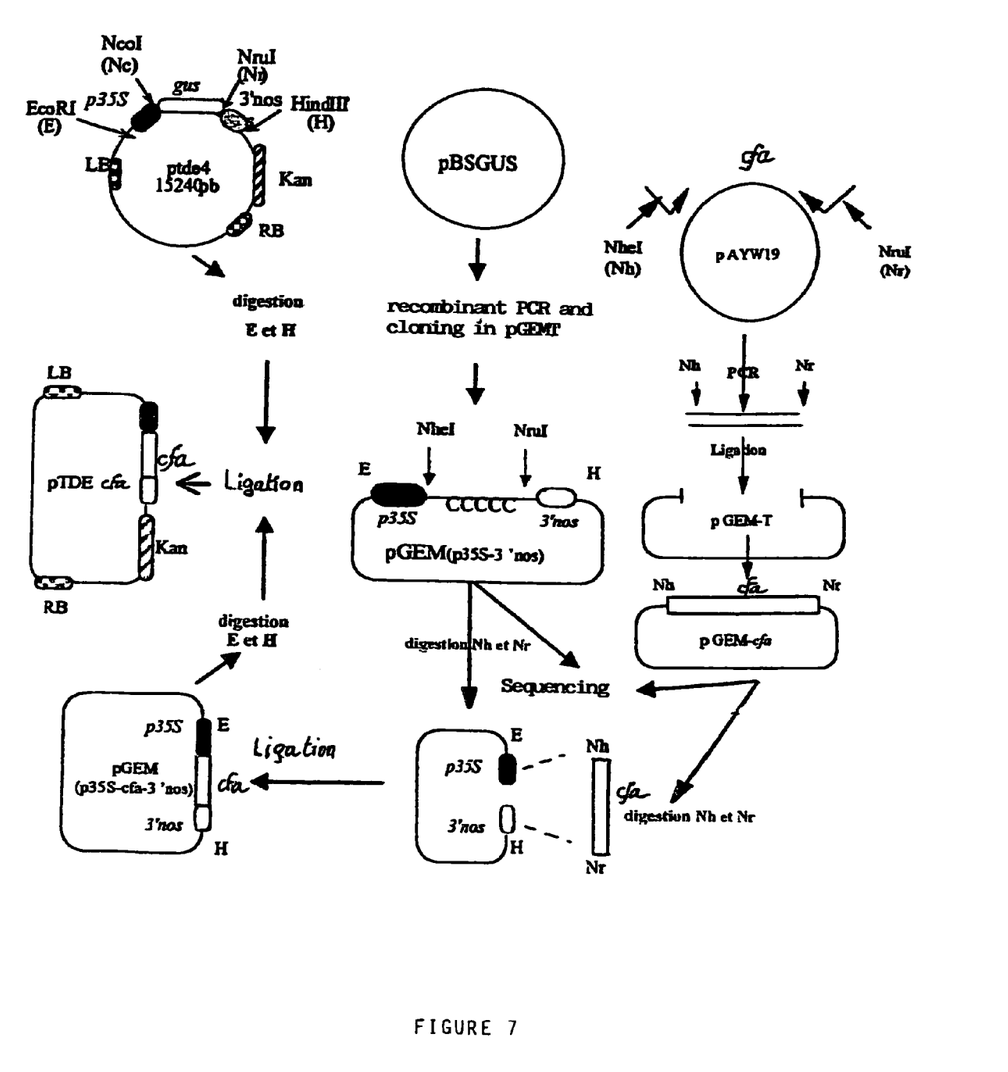
FIG. 7: Construction of the vector pTDEcfa

The binary vector is a vector comprising the LB and RB sequences of the plasmid Ti, necessary for gene transfer into plant cells by *Agrobacterium tumefaciens*. The binary vector pTDEcfa was constructed as follows (FIG. 7):

Cloning of the HindIII-EcoRI fragment derived from the vector pGEM(35S-cfa-3'nos)13 into the binary vector ptde4 from which the HindIII-EcoRI fragment has been removed. The vector obtained is called pTDEcfa. A selection was made among the clones obtained by using several restriction enzymes. We selected clone 8 to perform the triparental recombination The clone containing the vector pTDEcfa (clone 8) was used to prepare a quantity of DNA which was tested in a Southern blot experiment. In this experiment, the probe revealing the presence of the cfa gene by DNA-DNA hybridization was generated from the initial pAYW19 vector. As a result of this experiment we were able to verify by using different restriction enzymes that the cfa gene was indeed integrated in the binary vector between the 2 regulatory sequences: promoter and terminator.

The binary vector was then transferred to the bacterium *A. tumefaciens*, under the standard conditions.

Step 3: Transformation of the Plant

In a first phase, protoplasts, plant cells, tissues or tobacco plants are genetically transformed by the recombinant nucleic acids described above by the use of indirect transfer methods with the aid of a vector such as the *agrobacteria* (for example *Agrobacterium tumefaciens*: C58C1Rif: pGV2260; Deblaere et al., 1985) or by using direct transformation methods (electroporation, particle bombardment, infiltration under pressure, etc., (Kahl and Weising, 1993).

In the case where indirect gene transfer is used, the *agrobacteria* contain a plasmid possessing the vir regions (disarmed Ti plasmid) necessary for the transfer of the T-DNA into plant cells.

In a first optional step the cells are transformed by a recombinant nucleic acid (FIG. 3) coding for SAM synthetase. The transformants possessing a high methylating potential are then selected.

These lines or still untransformed cells are then genetically transformed in order to insert into their genome a recombinant nucleic aciid containing the gene coding for the CFA synthase described previously.

The protocol used to perform these transformations has been described by Van Lijsebettens et al. (1986 J. Mol. Biol., 188, 129–145) or itemized in the literature (Plant Genetic Transformatioon and Gene Expppression: A Laboratoryy Manual. Draper J., Scott R., Armitage P. and Walden R. Eds, Blackwell Scientific Publications, Oxford, 1988. Kahl G. and Weising K. (1993) Genetic Engineering of Plant Cells. In Biotechnology: Genetics Fundamentals and Genetic Engineering. Rehm H. J., Reed G., Pühler A and Stadler P. Eds, VCH Publishers Inc., New York (USA) vol. 2, pp 547–659).

In a particular example, the undifferentiated cells of tobacco variety BY2 were used for genetic transformation. These cells are maintained in vitro in liquid nutritive medium. Every 10 days, a 10 ml sample of cells is taken to inoculate 100 ml of medium in a 500 ml Erlenmeyer. The Erlenmeyer is placed in an orbital shaker at a speed of 140 rpm in the dark at 24° C. The transformation was performed on 3 days old cells. Two ml of cells are taken and inoculated with 100 µl of a culture of 24 h old transforming *agrobacteria*. The optical density at $\lambda=600$ nm of the agrobacterial culture used is adjusted to 1.5 units. The coculture of *agrobacteria*/plant cells is grown in small Petri dishes for 2 days at 24° C. and in the dark. After coculture, the plant cells are rinsed abundantly with nutritive medium in order to remove as many of the *agrobacteria* as possible. The plant cells are then placed in culture on a solid (gelified) medium. This medium contains cefotaxime to eliminate the remainder of the bacteria. It also contains kanamycin to permit the selection of the plant cells which have inserted the LB-RB fragment of the binary vector into their genome and which express the gene conferring resistance to kanamycin.

After 2 to 3 weeks of culture the plant cells resistant to kanamycin have developed. At this stage a sufficient quantity of biomass may be taken and placed in culture in liquid medium in order to accelerate the production of biomass, while maintaining the selection pressure (kanamycin-cefotaxime). After several cycles of culture we removed the selection pressure in the culture medium on a part of the biomass in order to be able to compare the lipid profiles of this suspension with those obtained from control cells cultured under the same conditions, without selection pressure.

By means of this method we have thus been able to obtain a cell suspension resistant to kanamycin. The presence of the gene coding for the CFA in the genetic material of this suspension was also confirmed. In order to do that, we performed extractions of DNA (Dellaporta et al., Plant Mol. Biol. Rep. 1 (1983) 19) followed by a PCR test using specific primers for the cfa gene. The positive result of the PCR shows the presence of a band of expected size corresponding to the cfa gene.

In another particular example, 0.5 cm diameter foliar disks were prepared from tobacco variety SR1 cultured in vitro and transformed. In brief, the disks were cultured for 24 h on a solid (gelified) cell dedifferentiation medium. They were then inoculated by immersion in a culture of 24 h old transforming *agrobacteria*, the optical density of which at $\lambda=600$ nm was adjusted to 1 unit.

Step 4: Culture and Selection of the Transformed Plants

The plant cells transformed by the vectors containing the constructions previously described are then regenerated from isolated cells, calluses or foliar disks by using the procedures usually used for plant cultures (Plant Cell Culture A Practical Approach. Dixon R. A. ed., IRL Press, Oxford, Washington D.C., 1985). The transformed cells and plants are placed in culture according to the usual procedures described in the literature. The transformed cells and plants are selected while being grown on a selective medium containing an antibiotic or toxin specific for the cassette introduced.

In a particular example, the foliar disks described above were sponged on sterile blotting paper, then placed in coculture for 2 days at 24° C. in the dark on the same solid cellular dedifferentiation medium. After coculture, the disks were rinsed for 0.5 hour in the bud induction medium, containing cefotaxime and kanamycin. Finally, the induction of the buds was accomplished on this same solid medium. Every week the disks were sampled, rinsed and replaced in culture on the same medium prepared extemporaneously.

After 4 to 5 weeks, the buds which develop are collected and placed in culture on a rooting medium containing cefotaxime and kanamycin.

Figure 8:
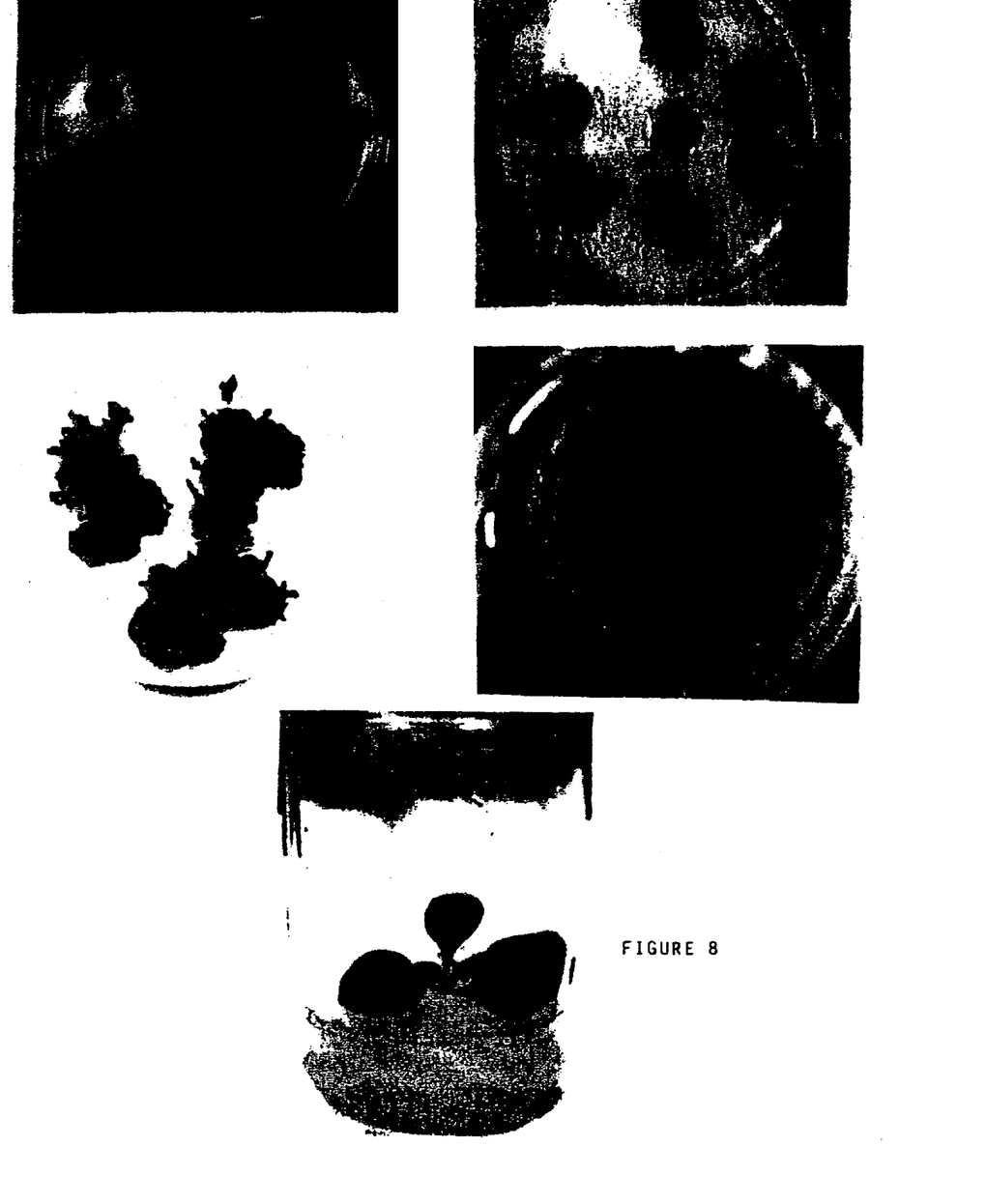
FIG. 8: Transformation of foliar disks and regeneration of the plants. A: *agrobacteria*-foliar disks coculture; B: 2nd week of culture; C: 5th week of culture; D: root system of the buds; E: plantlet cutting in vitro.

The different steps of this transformation are illustrated in FIG. 8.

About fifty buds were obtained by this method, about twenty of which had taken root on the selective medium. These plantlets are propagated by cuttings in order to produce sufficient biomass to conduct the PCR verifications which demonstrate the presence of the cfa gene and to extract the total lipids.

Step 5: Analysis of the Transformants

The transformants thus produced are then analyzed at several levels a)—Direct analysis confirming the presence of the gene in the plant cell or the plant, performed by either Southern blot or PCR analyses requiring extractions of genomic DNA (Protocol described in Sambrook and/or the Current Protocol).

Sambrook J., Fritsch E. F. and Maniatis T. in Molecular Cloning. A Laboratory Manual. Irwin N., Ford N., Nolan C. and Ferguson M. eds, Cold Spring Harbor Laboratory Press 1989.

Current protocols in Molecular Biology. Ausubel F. M., Brent R., Kingston R. E., Moore D. D., Seidman J. G., Smith J. A. and Struhl K eds, Current Protocols Inc Willey, Mass. . . ., vol 1: Molecular Biology—Techniques. 1994 and vol. 2: Molecular Biology—Laboratory. 1994.

b)—Analysis of the gene product i.e. mRNA by Northern blot, confirming the transcription of the gene (Protocol described in Sambrook and/or the Current Protocol cited above)

c)—Analysis of the protein synthesized, i.e. the enzyme (confirming the translation of the gene into protein) and providing a check on the functionality of the latter (immunoblot enzymatic assay, Western blot).

The assay of SAM snythetase and the SAM pool in the cells is performed more particularly by following the protocol described by Mathur and Sachar (1981 FEBS Lett., 287, 113–117)

The assay of the CFA synthase in tobacco cells and plants is performed according to the protocol described by Taylor and Cronan (1979 Biochemistry, 18, 3292–3300).

d)—The analysis and the identification of the triglycerides synthesized are conducted by using chromatographic procedures of the HPLC and GC-MS type or by NMR after extraction by following the protocols described in the literature.

These experiments permit verification that the recombinant nucleic acids are functional, that they may be introduced into plant cells, that said cells may be regenerated and that these cells actually produce branched fatty acids. These acids may then be recovered directly in the seeds of the corresponding plants by known extraction techniques.

In a particular example, the lipids were extracted from the plants obtained above (seeds, leaves or cell suspensions) by using the procedure described by Browse et al. (Anal. Biochem. 152 (1986) 141). The lipids obtained were transesterified by the method of Fisher and Cherry (Lipids 18 (1983) 589). This method uses 20% tetramethyl ammonium hydroxide in methanol. It is non-destructive, efficient and lends itself perfectly to the methanolysis of unusual oils. The fatty acid methyl esters thus obtained were analyzed by gas chromatography.

The lipid analyses were first performed on extracts of transformed and untransformed BV2 cell suspensions, both types being cultured for 7 days under the same conditions (medium without selection pressure, shaking at 140 rpm, 24° C., in the dark). These analyses were used to validate the method of extraction of the total lipids in the cell suspensions.

Subsequently, the comparison of the lipid extracts obtained from BY2 cell suspensions and from SR1 tobacco leaves transformed and untransformed under different conditions (with or without selection pressure, in the presence or absence of light, 7 or 14 days old) demonstrates the presence of compounds having the structure of branched fatty acids according to the invention in the transformed plant material.

The mass spectrometric analysis of the samples obtained confirms that the fatty acids obtained indeed include branched fatty acids in the sense of the invention, i.e. possessing at least one non-cyclic substitution. These results show in particular the presence of 9 (and/or 10)-methyl octadecanoic acid and/or 9 (and/or 10)-methyl hexadecanoic acid.

Step 6: Treatment of the Branched Fatty Acids

In an optional step, the branched fatty acids produced by the plant materials of the invention are treated so as to improve their physicochemical properties, in particular their lubricant properties.

In a particular example, this treatmentt comprises the hydrogenation of the fatty acids in order to increase the proportion of branched fatty acids and thus to obtain compositions having a enhanced resistance to oxidation and low pour points. This hydrogenation is performed under conditions known to the specialist skilled in the art.

EXAMPLE B

Construction of a Genetically Modified Plant Cell Capable of Producing Branched (Multibranched) Fatty Acids During Elongation This example illustrates the construction of genetically modified plants capable of producing multibranched fatty acids. In particular, this example describes the insertion into the genome of the plant by genetic engineering a gene or a set of genes leading the plant to use a non-linear acyl-CoA with more than 3 carbon atoms (methylmalonyl CoA for example) instead of malonyl CoA in order to obtain branched fatty acids called multibranched fatty acids such as 2, 4, 6, 8-tetramethyl decanoic acid. Since the synthesis of the fatty acids occurs in the chloroplasts, the recombinant nucleic acid inserted advantageously comprises a gene coding for a malonyl-CoA decarboxylase (E.C. No. 4.1.1.9.) such that this enzyme is active in the chloroplast or at another level of the cell. This obtained either by introduction of the recombinant nucleic acid into the chloroplasts or by insertion of a transit peptide permitting the address of the protein in this compartment.

Figure 9:
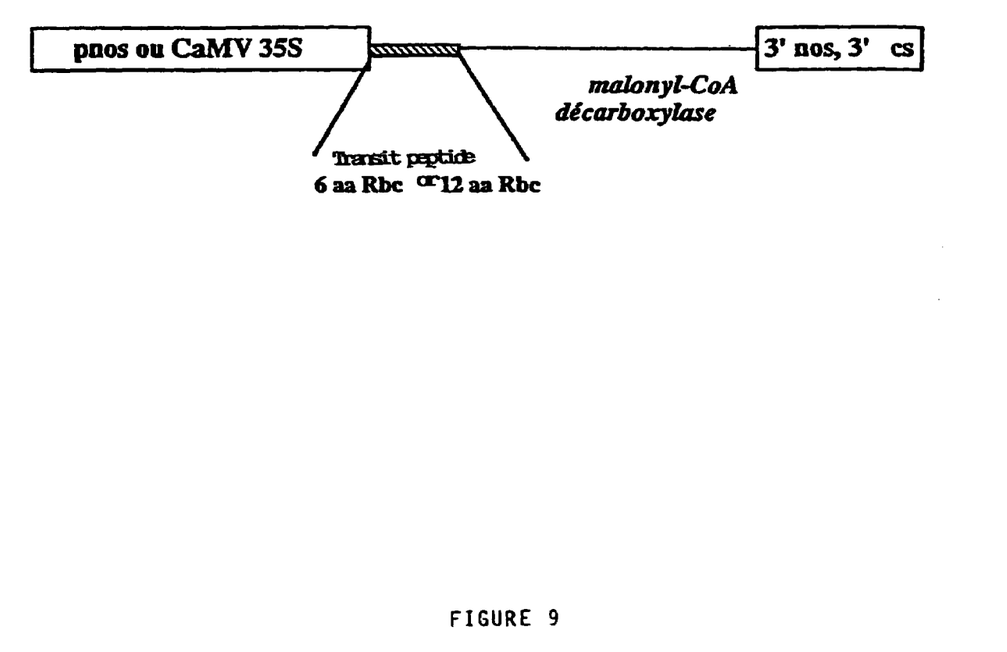
FIG. 9: Representation of a recombinant nucleic acid comprising a gene coding for malonyl-CoA decarboxylase.

The construction of these transgenic plants according to the invention is achieved according to the following steps (FIG. 9).

Step 1: Plant Material Used

The plant material used is identical with that described in example A.

Step 2: Genic Constructions

The genetic transformation consists of introducing an expression cassette comprising the gene to be transferred, the promoter permitting expression of this gene which may be constitutive, spatial or temporal and an additional nucleotide sequence coding for a transit peptide allowing the protein to be addressed to a cell compartment where it will be active.

2.1. Selection and Isolation of the Nucleic Acids Coding for the Enzymes.

Use of the gene coding for malonyl-CoA decarboxylase whose nucleotide sequence has been described by Kolattukudy et al. (1987) or all other analogous nucleotide sequences derived from other prokaryotic or eukaryotic organisms or micro-organisms.

Kolattukudy P. E., Rogers L. M., Poulose A. J., Jang S. H., Kim Y. S., Cheesbrough T. M. and Liggitt D. H. (1987) Developmental pattern of the expression of malonyl-CoA decarboxylase gene and the production of unique lipids in the goose uropygial glands. Arch. Biochem. Biophys., 256, 446–454.

Fernandese N. D. and Kolattukudy P. E. (1996) Cloning, sequencing and characterization of a fatty acid synthase-encoding gene from *Mycobacterium tuberculosis* var. *bovis* BCG. Gene, 170, 95–99.

In certain cases, components of fatty acid synthesis are localized in the chloroplasts or other organelles. In our case, the enzyme synthesized: malonyl-CoA decarboxylase, must be transported into the chloroplasts to be active. It will be necessary to add to our genic constructions a DNA sequence coding for an operational transit peptide recognized by the receptor plant. These transit peptides are usually leader sequences which will need to be combined with the nucleotide sequence of the gene associated with a specific promoter. These "signal" sequences may be represented by any other nucleotide sequences derived from that of a gene which is expressed in the cytoplasm before reaching its appropriate reaction compartment. The DNA for these transit peptides may be derived from other plants. It may be, for example, the transit peptide of the small subunit of the RUBISCO of soya or the sequences coding for the 6 or 12 terminal amino acids of the mature small subunit of the RUBISCO of pea and cited in the patent by Calgene WO 94/29467 (schema of type 4).

2.2. Selection of the Promoter Regions

In this example, the promoters used are the 35S promoter of the cauliflower mosaic virus and the promoter of the gene for nopaline synthase (nos). The structure of these promoters has been described for example by Benfey and Chua (1990, Science, 250, 959–966).

2.3. Selection of the Transcription Terminating Regions

In this example, the transcription terminating regions used are derived from the genes for nopaline synthase (nos) and octopine synthase (ocs) (FIG. 9).

2.4. Construction of the Recombinant Nucleic Acids (Vectors)

In order to construct the recombinant nucleic acids which enable the above elements to be introduced into the plant cells, these genetic elements are first isolated and subcloned into pBR322 and pUC type cloning vectors, which bear markers permitting the selection of the transformants which acquire resistance to cytotoxic agents such as antibiotics, toxins, etc. The expression cassettes are then introduced into binary vectors containing the sequences necessary for the transformation of plants, in particular, the T-DNA vector. This vector is used for the transformation of the plants and the structure of the vectors containing the specific recognition sequences RB and LB) has been extensively described in the literature. (Book by Hoekema, the Binary Plant Vector Systems, Offsetdrukkerij Kanters B. V., Alblasserdam, 1985. Molecular Genetics of the Bacteria-Plant Interaction, Puhler A., Ed., Sprinnger-Verlag, NY, 1983. Plant Genetic Transformation and Gene Expression: A Laboratory Manual Draper J., Scott R., Armitage P. and Walden R. Eds, Blackwell Scientific Publications, Oxford, 1988. Kahl G. and Weising K. (1993) Genetic Engineering of Plant Cells. In Biotechnology: Genetics Fundamentals and Genetic Engineering. Rehm H. J., Reed G., Pühler A and Stadler P. Eds, VCH Publishers Inc., New York (USA) vol. 2, pp 547–659).

The structure of the recombinant nucleic acids thus prepared is shown in FIG. 9.

Step 3: Transformation of the Plant

In a first phase, protoplasts, plant cells, tobacco plants or tissues thereof are genetically transformed by the recombinant nucleic acids described above by use of indirect transfer methods using a vector such as the *agrobacteria* (for example, *Agrobacterium tumefaciens*: C58C1Rif: pGV2260; Deblaere et al., 1985) or by using direct transformation methods (electroporation, particle bombardment, infiltration under vacuum, etc., (Kahl and Weising, 1993).

In the case of the indirect gene transfer, the *agrobacteria* contain a plasmid possessing the vir regions (disarmed Ti plasmid) necessary for the transfer of the T-DNA into the plant cells.

The cells are genetically transformed in order to insert into their genome a recombinant nucleic acid (FIG. 9) containing the gene coding for the malonyl-CoA decarboxylase previously described.

The protocol used to perform these transformations has been described by Van Lijsebettens et al. (1986 J. Mol. Biol., 188, 129–145) and itemized in the literature. (Plant Genetic Transformation and Gene Expression: A Laboratory Manual Draper J., Scott R., Armitage P. and Walden R. Eds, Blackwell Scientific Publications, Oxford, 1988. Kahl G. and Weising K. (1993) Genetic Engineering of Plant Cells. In Biotechnology: Genetics Fundamentals and Genetic Engineering. Rehm H. J., Reed G., Pühler A and Stadler P. Eds, VCH Publishers Inc., New York (USA) vol. 2, pp 547–659).

Step 4: Culture and Selection of the Transformed Plants.

The plant cells transformed by the vectors containing the constructions previously described are then regenerated from isolated cells, calluses or foliar disks by using the usual procedures for plant cultures (Pllant Cell Culture: A Practical Approach. Dixon R. A. ed., IRL Press, Oxford, Washington D.C., 1985). The transformed cells and plants are placed in culture in accordance with the usual procedures described in the literature. The transformed cells and plants are selected during their culture on a selective medium containing an antibiotic or toxin specific for the cassette introduced.

Step 5: Analysis of the Transformants

The transformants thus produced are then analyzed at several levels a)—Direct analysis confirming the presence of the gene in the plant cell or the plant, performed by either Southern blot or PCR analyses requiring extractions of genomic DNA according to a Protocol described in:

Sambrook J., Fritsch E. F. and Maniatis T. in Molecular Cloning. A Laboratory Manual. Irwin N., Ford N., Nolan C. and Ferguson M. eds, Cold Spring Harbor Laboratory Press 1989 or, Current protocols in Molecular Biology. Ausubel F. M., Brent R., Kingston R. E., Moore D. D., Seidman J. G., Smith J. A. and Struhl K eds, Current Protocols Inc Wiley, Mass. . . ., vol 1: Molecular Biology—Techniques. 1994 and vol. 2: Molecular Biology—Laboratory. 1994.

b)—Analysis of the gene product i.e. mRNA by Northern blot, confirming the transcription of the gene (Protocol described in Sambrook and/or the Current Protocol cited above)

c)—Analysis of the protein synthesized, i.e. the enzyme (confirming the translation of the gene into protein) and providing a check on the functionality of the latter (immunoblot enzymatic assay, Western blot).

d)—The assay of malonyl-CoA decarboxylase according to the protocol described by Kolattukudy et al. (1987): Developmental pattern of the expression of malonyl-CoA decarboxylase gene and the production of unique lipids in the goose uropygial glands. Arch. Biochem. Biophys., 256, 446–454.

e)—The analysis and the identification of the triglycerides synthesized are conducted by using chromatographic procedures of the HPLC and GC-MS type or by NMR after extraction by following the protocols described in the literature.

These experiments permit verification that the recombinant nucleic acids are functional, that they may be introduced into plant cells, that said cells may be regenerated and that these cells actually produce branched fatty acids. These acids may then be recovered directly in the seeds of the corresponding plants by known extraction techniques.

The invention claimed is:

1. A process for producing branched fatty acids, comprising:
   a. introducing a recombinant nucleic acid coding for a cyclopropane fatty acid synthase into a plant cell, a plant tissue or a seed of a plant;
   b. regenerating a transgenic plant from the plant cell, the plant tissue or the seed of the plant wherein said transgenic plant produces branched fatty acids; and
   c. recovering said branched fatty acids from said transgenic plant.

2. The process according to claim 1, further comprising the step of extracting the branched fatty acids.

3. The process according to claim 1, wherein said recombinant nucleic acid further comprises a plant expressible promoter selected from the group consisting of a nopaline synthase promoter (nos), an octopine synthase promoter (ocp), a mannopine promoter, an agropine promoter, a napine promoter and an acyl carrier protein promoter (ACP).

4. The process according to claim 3, wherein the promoter expresses the nucleic acid in a seed of a plant.

5. A process for preparing branched fatty acids from a transgenic plant whose cells contain a recombinant nucleic acid comprising in the following order:
   a. a plant expressible promoter selected from the group consisting of a nopaline synthase promoter (nos), an octopine synthase promoter (ocp), a mannopine promoter, an agropine promoter, a napine promoter and an acyl carrier protein promoter (ACP);
   b. a nucleic acid coding for a cyclopropane fatty acid synthase; and
   c. a 3' transcription termination sequence, comprising:
      culturing said transgenic plant in a field;
      recovering the seeds from said transgenic plant; and
      extracting the branched fatty acids from these seeds.

6. The process according to claim 1 or claim 5, wherein said transgenic plant is colza, sunflower, peanut, soya, flax or maize.

7. A process for producing branched fatty acids, comprising:
   introducing a recombinant nucleic acid coding for a cyclopropane fatty acid synthase into a plant cell;
   culturing said plant cell in a medium suitable for growth; and
   extracting and purifying the branched fatty acids from said plant cell or from the supernatant of said medium.

8. A process for producing branched fatty acids, comprising:
   a. introducing a recombinant nucleic acid coding for a cyclopropane fatty acid synthase into a tobacco cell, a tobacco tissue or a tobacco seed;
   b. regenerating a transgenic plant from the tobacco cell, the tobacco tissue or the tobacco seed, wherein said transgenic plant produces branched fatty acids; and
   c. recovering said branched fatty acids from said transgenic plant.

* * * * *